(12) United States Patent
Brandmayr et al.

(10) Patent No.: US 9,566,016 B2
(45) Date of Patent: Feb. 14, 2017

(54) METHOD FOR VISUALIZING MULTI-CHANNEL SIGNALS

(75) Inventors: Georg Brandmayr, Vienna (AT); Hubert Egger, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 802 days.

(21) Appl. No.: 13/057,868

(22) PCT Filed: Jul. 8, 2009

(86) PCT No.: PCT/EP2009/004935
§ 371 (c)(1),
(2), (4) Date: Feb. 7, 2011

(87) PCT Pub. No.: WO2010/015305
PCT Pub. Date: Feb. 11, 2010

(65) Prior Publication Data
US 2011/0134139 A1    Jun. 9, 2011

(30) Foreign Application Priority Data

Aug. 7, 2008  (DE) .................. 10 2008 036 714

(51) Int. Cl.
*G06T 11/20* (2006.01)
*G09G 5/02* (2006.01)
(Continued)

(52) U.S. Cl.
CPC .......... *A61B 5/04888* (2013.01); *A61B 5/486* (2013.01); *A61B 5/743* (2013.01); *G06T 11/206* (2013.01);
(Continued)

(58) Field of Classification Search
CPC .......... G09G 5/02; G09G 5/06; G06T 11/001; G06T 11/206; G06F 3/0481; G06F 17/246; A61B 5/04085; A61B 5/6831; A61B 5/0006
(Continued)

(56) References Cited

U.S. PATENT DOCUMENTS 5,085,225 A *  2/1992  DeLuca et al. ............... 600/546
5,341,813 A *  8/1994  Teare et al. ................... 600/546
(Continued)

FOREIGN PATENT DOCUMENTS

DE        19521464 A1    3/1997
EP        1240864 A1     9/2002
(Continued)

OTHER PUBLICATIONS

PCT International Search Report for International Application No. PCT/EP2009/004935, mailed Oct. 2, 2009.

*Primary Examiner* — Ulka Chauhan
*Assistant Examiner* — Saptarshi Mazumder
(74) *Attorney, Agent, or Firm* — Holland & Hart

(57) ABSTRACT

The invention relates to a method for visualizing multi-channel sensor signals, especially myoelectric signals, which are derived from a limb or an amputation stump by way of electrodes, comprising the following steps: a display direction and a display amount are associated with each sensor signal, the display direction represents exactly one sensor signal, the display amount represents the intensity of the respective signal, the display direction and the display amount of all sensor signals are presented simultaneously in real time on a display device as a graphical object.

12 Claims, 2 Drawing Sheets

(51) Int. Cl.
- *A61B 5/0488* (2006.01)
- *A61B 5/00* (2006.01)
- *G09G 5/06* (2006.01)
- *G06T 11/00* (2006.01)

(52) U.S. Cl.
CPC ............... *G06T 11/001* (2013.01); *G09G 5/02* (2013.01); *G09G 5/06* (2013.01)

(58) Field of Classification Search
USPC ............... 345/440, 619, 156, 441, 666, 589; 600/546, 382
See application file for complete search history.

(56) References Cited

U.S. PATENT DOCUMENTS

| | | | |
|---|---|---|---|
| 6,047,202 A * | 4/2000 | Finneran et al. | 600/382 |
| 7,563,234 B2 * | 7/2009 | Cordo | 601/5 |
| 2002/0143405 A1 * | 10/2002 | Davalli et al. | 623/24 |
| 2008/0101536 A1 * | 5/2008 | Sendai | 378/22 |
| 2009/0171233 A1 * | 7/2009 | Lanfermann et al. | 600/546 |
| 2011/0137196 A1 * | 6/2011 | Kakei et al. | 600/546 |

FOREIGN PATENT DOCUMENTS

| | | |
|---|---|---|
| JP | 2004-024769 | 1/2004 |
| WO | 03005887 A2 | 1/2003 |
| WO | 2007141680 A1 | 12/2007 |

\* cited by examiner

METHOD FOR VISUALIZING MULTI-CHANNEL SIGNALS

The invention relates to a method for visualizing multichannel sensor signals, more particularly myoelectric signals, which are tapped by electrodes from a limb or an amputation stump.

Driven prosthesis, i.e. prostheses that comprise a motor drive in order to displace components with respect to one another, require control signals for the drives to work as desired. An option for this consists of tapping myoelectric signals by electrodes and using these as impulses for activating or deactivating drives via a control apparatus, after possibly necessary amplification. In order to generate meaningful myoelectric signals, muscles or muscle remains after amputation must be contracted. The contraction pattern can then be used to generate corresponding signals, by means of which the drives are moved. Such a myoelectric prosthesis control can be used for humans with amputations or dysmelia. In principle, a corresponding myoelectric control of driven orthoses is likewise possible.

As the movements of the prostheses or orthoses are intended to become more complex, the number of the required signals increases. Whereas mere opening and closing of a gripper requires only two signals, the number of the required signals increases with a corresponding increase in the number of functions that can be implemented. The increase in the number of signals can be brought about by an increase in the contraction patterns and/or an increase in the number of electrodes. Irrespective of this, a patient finds it difficult to tense muscles or muscle remains in a targeted fashion without optical feedback. Uninjured humans see how their extremities react to their will of moving the extremities in a certain fashion. If a muscle is tensed, for example the biceps on the arm, the person sees and feels a movement of the forearm. In particular, visible feedback, in the form of movement, of thought contraction commands can improve coordinative abilities. The optical feedback no longer exists if limbs are missing. Such patients do not see any consequences of their movement will although the latter is present and does in fact cause a contraction of the muscles or the muscle remains. The perception of a differentiated, reproducible consequence as a result of a movement will and a muscle contraction is extraordinarily important in the case of rehabilitation measures and in the prosthetic aid of patients.

It is an object of the invention to provide a simple and meaningful interpretation of a movement will, in particular for a non-existent limb. According to the invention, this object is achieved by a method with the features of the main claim. Advantageous embodiments and developments of the method are listed in the dependent claims.

The method for visualizing multichannel sensor signals, recorded from the body in order to register the muscle activity, e.g. myoelectric signals that are tapped from a limb or an amputation stump by electrodes, provides for each signal to be assigned a display direction and a display magnitude. The display direction represents precisely one signal, e.g. an electrode signal; the display magnitude represents the intensity of the signal, i.e. the intensity of the motor activity of the respective muscle or of the nerve thereof, e.g. the contraction intensity of the respective muscle, which is assigned to the sensor or to the electrode. The display direction and the display magnitude of all sensor signals are simultaneously illustrated in real time on a display instrument as a graphical object, and so the movement will is reproduced in the form of assignable, reproducible shapes. The patient receives direct visual feedback because all signals are displayed in real time on a display instrument, more particularly on a screen. Respectively different movement wills, for example "clench fist" or "bend the wrist", generate different objects, which can differ in both shape and size. By displaying the graphical object, which is displayed in real time on a display instrument as a function of the type and intensity of the motor activity or the muscle contraction, there is direct feedback of the movement will in visual form. The patient sees what he/she would like to perform or would do if the limb were unaffected.

The graphical object is preferably illustrated as a two-dimensional graph, more particularly as a polygon, because such a two-dimensional illustration can very easily be digested by a patient. Such simple geometric shapes, i.e. polygons, provide a substantially improved overview compared to superposed curves that show an electrode intensity as a function of time. Moreover, the illustration as a graphical object provides high levels of recognition, with, at the same time, the option of being able to display a multiplicity of electrode signals. The illustration of the movement will simplifies the reproducibility of the contraction pattern.

A development of the invention provides for reference objects to be displayed on the display instrument at the same time as the graphical object. This affords the possibility of practicing certain target contractions and giving the patient the option of modifying the current contraction until it corresponds to the reference contraction or becomes similar to the latter. The reference objects can either be prescribed or be stored during preceding analysis sessions, and can be used for parameterizing a prosthesis control or an orthosis control. Discovered or set reference contractions or reference patterns are illustrated at the same time as the current contraction pattern, as a result of which both the patient and a prosthetist or medical practitioner can examine the reproducibility and deviations. As a result, the contractions can be trained and further differentiated by the patient in a targeted fashion. In addition, the contraction patterns can be visualized in parallel with an activation of a prosthesis or orthosis, as a result of which it is possible, at the same time, to identify what object causes what movement of the prosthesis or orthosis. Thus, a deviation between the actual contraction, the reference contraction and the action of the prosthesis or orthosis can be visualized and there can be feedback; this can be brought about for there to be an improvement in the control quality.

So that the reference object can be distinguished in an improved fashion, it is displayed in a different color and/or with a different intensity than the graphical object, and so it is easier to bring about an association between the current contraction and the desired contraction or reference contraction. In principle, the reference object and/or the graphical object can also be accentuated in terms of color or intensity if the registered contraction pattern matches the references pattern or is sufficiently close to the latter. This shows the patient that the contraction provides sufficient clarity for movement intent.

The display magnitude can be normalized in order to illustrate the influence of the contraction intensity on the object shape in a clear and immediately visible fashion.

In addition to tapping the sensor signals by surface electrodes, it is also possible to use signals from electromyography sensors, nerve sensors, pressure sensors and/or strain sensors in order to register the motor activity.

In the following text, the method will be explained in more detail on the basis of attached figures, in which.

Figure 1:
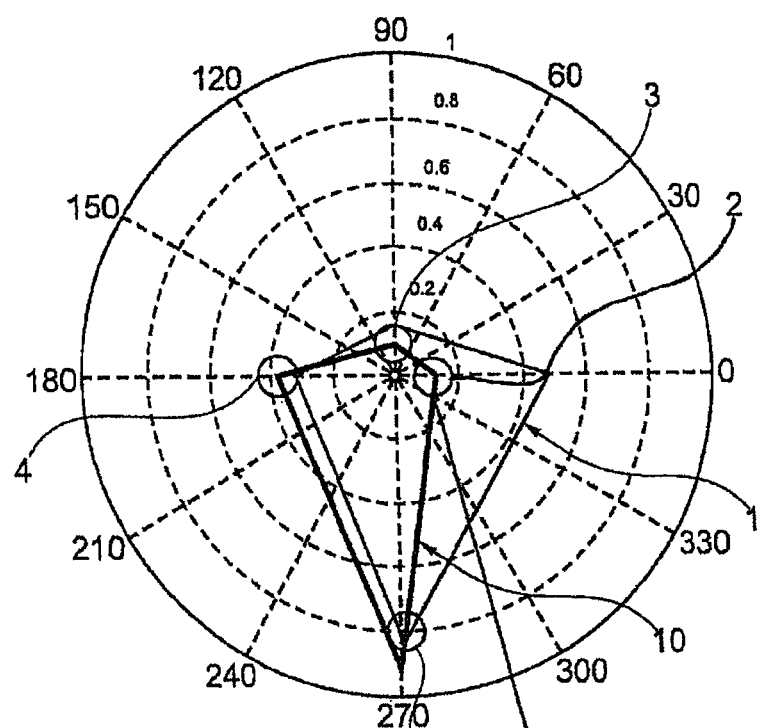
FIG. 1 shows a first illustration of an illustration with reference contraction and a contraction tapped by four electrodes.

FIG. 1 illustrates a graphical object 1, which reproduces a current contraction of muscle groups. Four electrodes for tapping myoelectric signals were arranged on the limb, which is a forearm in the present case. Here, each electrode represents one corner 2, 3, 4, 5, by means of which the graphical object 1 representing the current contraction is illustrated. In the present exemplary embodiment, the graphical object 1 forms a quadrilateral, with each corner 2, 3, 4, 5 being assigned a display direction. In the present exemplary embodiment, the display directions correspond to crossing axes, and so the first electrode is assigned to the axis projecting from the origin at 0°, the second electrode 3 is assigned to the axis at 90°, the third electrode 4 is assigned to the axis at 180° and the fourth electrode 5 is assigned to 270°. The respective corners 2, 3, 4, 5 are interconnected by lines, and so the graphical object 1 forms a quadrilateral. The distance of the corners 2, 3, 4, 5 from the origin specifies the intensity of the contraction. If the electrode assigned to the first corner 2 is not supplied with a myoelectric signal, i.e. if the muscle assigned to the electrode is not being contracted, the first corner 2 is at the origin or very close thereto; if there is an intensive contraction, the first corner 2 is moved further outward. The illustration of the tapped electrode signals in the form of the graphical object 1 is brought about in real time, and so a patient obtains the visual feedback, without time delay, as to how the current muscle contraction looks on the display instrument.

A reference object 10, which is constantly displayed on the display instrument, is likewise illustrated. This reference object 10 is illustrated in a different color and/or with a different intensity than the graphical object 1 of the current contraction. In the illustrated exemplary embodiment, the current contraction quite closely approximates the reference object; only the electrode represented by the first corner 2 has a deflection that is too strong, and so the associated muscle is contracting too strongly.

Figure 2:
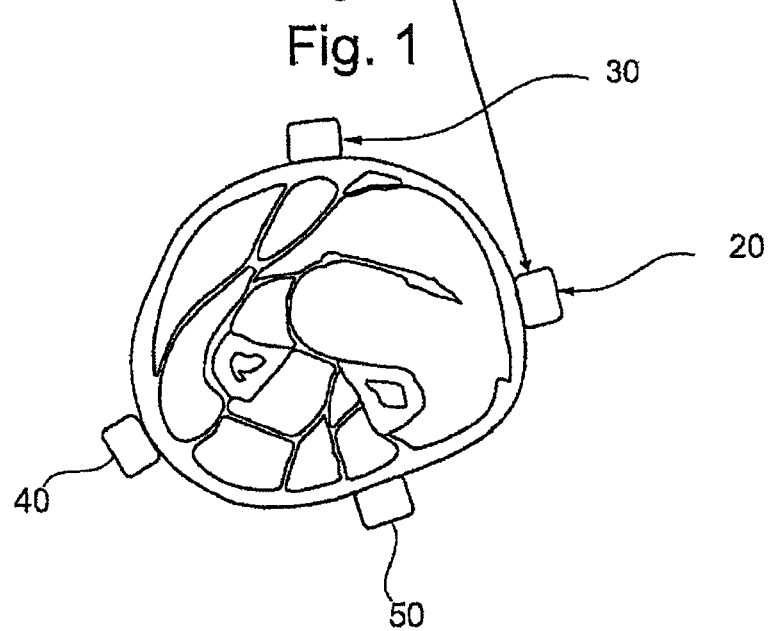
FIG. 2 shows an anatomical interpretation of the electrode arrangement as per FIG. 1.

FIG. 2 shows an anatomical interpretation of the above-described illustration. Each corner 2, 3, 4, 5 is associated with an electrode 20, 30, 40, 50, which is respectively attached to a forearm. The arrangement of the electrodes can be gathered from the schematic slice image through the forearm with the corresponding muscles. This anatomical interpretation of the signals affords the possibility of modifying the arrangement of the electrodes as a function of the actually established signals or of teaching the patient to practice different movement patterns and muscle contraction patterns. An object of the invention is to provide a control of a prosthesis or an orthosis that is matched to the patient. To this end, it is necessary for different contraction patterns to be registered by the patient in a reproducible fashion such that, for example, after the thought command "clench fist", a reproducible contraction pattern is generated, which leads to a corresponding prosthesis control such that a prosthetic hand is closed.

The position and signal intensity of each electrode 20, 30, 40, 50 determines one corner of the object 1. Together, all corners define the graphical object 1. The object 1 maintains its shape for a certain movement or a certain contraction pattern even if the magnitudes are changed by the same amount. It is merely scaled in size. A change in shape occurs if the magnitudes are changed unevenly. The electrode signals are no longer illustrated over time, as disclosed by the prior art; as a result, the complexity for the observer is reduced. The prior art has disclosed the illustration of the electrode signals as superposed graphs with respect to time. Each graph usually has its own color for improved differentiation. Two or three signals can still be registered as a contraction pattern, but this becomes substantially more difficult for larger numbers of signals and electrodes. Moreover, it is not possible to illustrate a reference contraction in respect of time-dependent curves. It is likewise difficult to achieve a graphical separation of the contraction strength and the type of contraction. Previously, complex, threshold-based rules were applied to classify a contraction pattern; the manual evaluation of these in the time graph is extraordinarily laborious. Assessing the contractions is only made possible by a prosthesis error function. By contrast, time is no longer illustrated in the illustrated invention, as a result of which the complexity of the perception for the observer is reduced.

As illustrated in the example in FIG. 1, this object preferably consists of a plurality of corners, with there being one corner for each electrode. This polygon can be interpreted as a contraction pattern intuitively and at a glance, without technical understanding, schooling or other previous knowledge; as a result, even the movement will is provided with visual feedback. The invention returns the visual consequence of the movement will of the patient to the latter, as a result of which said patient's actions, namely the contraction of the muscles, can be matched and differentiated in a targeted fashion. Moreover, the illustration allows the evaluation and the training of the reproducibility of the contraction pattern, and so reliable classification with a low error count in the prosthesis control can be achieved, and, with this, also an unprecedented level of acceptance of the prosthesis or orthosis.

If the electrodes are spatially positioned in the same order as the signal illustration, as is the case in FIGS. 1 and 2, this also allows conclusions to be drawn in respect of the anatomy. Thus, for example, the extent of crosstalk between two adjacent signals can be registered, or contraction patterns can be ascribed to the generator muscles thereof on the basis of slice images.

Moreover, patients with malformations, who, in contrast to amputation patients, naturally do not have phantom perception, are only able to learn a differentiated contraction, and hence a movement will, with the aid of the invention. The visual feedback allows patients with dysmelia to approach a desired contraction pattern and hence an actual movement, as a result of which an expedient, differentiable contraction is learnt.

Figure 3:
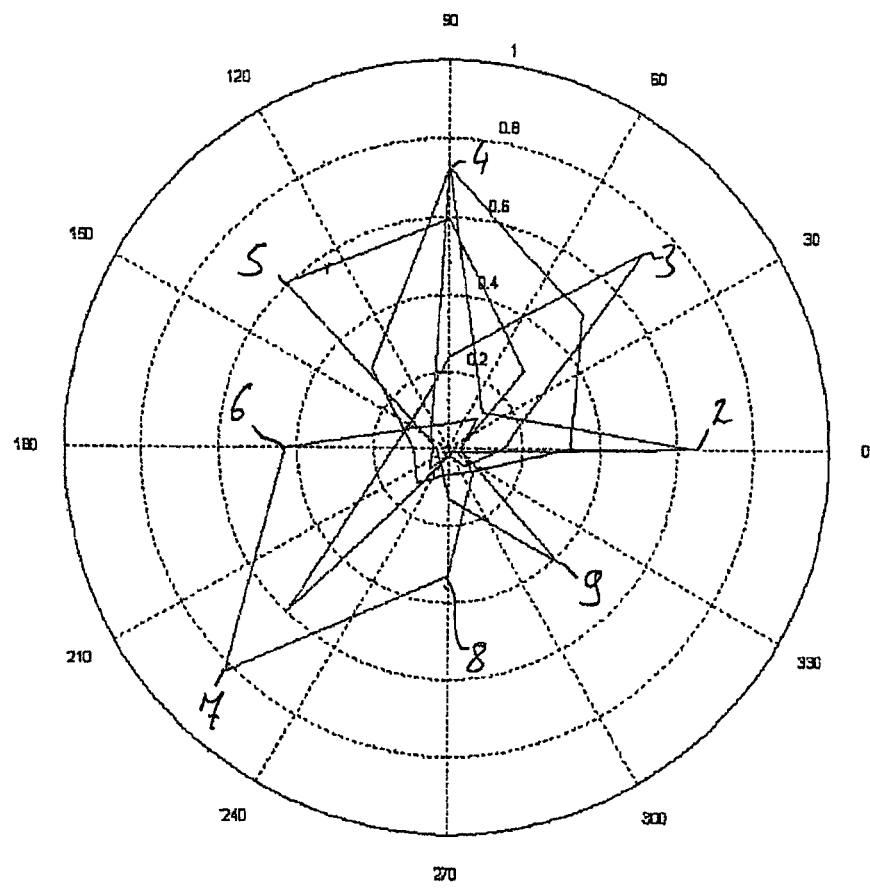
FIG. 3 shows generated reference contractions for eight electrodes.

FIG. 3 illustrates five reference contractions that were generated on the basis of eight electrodes. The person who produced the reference contractions can train their contraction patterns on the basis of said reference contractions.

The illustration of a contraction pattern as a single object allows a patient to evaluate all signals directly and without technical understanding. The patient him/herself or a prosthetist or a person skilled in the art can identify the movement intent of the patient directly from the illustration as a single graphical object for the purposes of adjusting a prosthesis control or orthosis control. The illustrated object is preferably a polygon, but it can also be provided as a three-dimensional illustration, the shape of which corresponds to the contraction pattern, i.e. the type of desired movement, and the size of which corresponds to the contraction strength, i.e. the intensity of the muscle tension.

The invention claimed is:

1. A method for visualizing multichannel sensor signals for registering muscle activity, comprising the following steps:
   collecting the signals using electrodes in contact with a limb or amputation stump wherein each signal is assigned a display direction and a display magnitude, the display direction representing precisely one signal and the display magnitude representing the intensity of the motor activity of either the respective muscle or the nerve thereof;
   simultaneously illustrating the display direction and the display magnitude of all signals in real time on a display instrument as a graphical object;
   displaying reference objects on the display instrument at the same time as the graphical object, the reference objects being derived from reference contractions obtained during previous reference contractions in the respective muscle.

2. The method as claimed in claim 1, wherein the graphical object is illustrated as a two-dimensional graph.

3. The method as claimed in claim 1, wherein the reference object is displayed in a different color, with a different pattern and/or with a different intensity than the object.

4. The method as claimed in claim 1, wherein the display magnitude is normalized.

5. The method as claimed in claim 1, wherein a prosthesis apparatus or orthosis apparatus is controlled by the signals at the same time as the visualization.

6. The method as claimed in claim 1, wherein myoelectric signals, signals from electromyography sensors, nerve sensors, pressure sensors and/or strain sensors are used as sensor signals.

7. A method for visualizing multi channel sensor signals, comprising:
   providing a display and a plurality of electrodes in contact with a limb or amputation stump;
   sensing activity with the electrodes in a muscle of the limb or amputation stump or a nerve of the muscle, and generating signals;
   assigning a display direction and a display magnitude to each signal, the display direction representing a single signal, the display magnitude representing an intensity of a motor activity of the muscle or nerve, the display direction and display magnitude of all signals being simultaneously illustrated in real time on the display as a graphical object;
   displaying reference objects on the display at the same time as the graphical object, the reference objects being derived from reference contractions obtained during previous contractions in the respective muscle.

8. The method as claimed in claim 7, further comprising illustrating the graphical object as a two-dimensional graph.

9. The method as claimed in claim 7, further comprising displaying the reference object in a different color, with a different pattern and/or with a different intensity than the object.

10. The method as claimed in claim 7, further comprising normalizing the display magnitude.

11. The method as claimed in claim 7, further comprising controlling a prosthesis apparatus or orthosis apparatus by the signals at the same time as the visualization.

12. The method as claimed in claim 7, further comprising using myoelectric signals, signals from electromyography sensors, nerve sensors, pressure sensors and/or strain sensors as sensor signals.

* * * * *